US005760076A

United States Patent [19]
Vazquez et al.

[11] Patent Number: 5,760,076
[45] Date of Patent: Jun. 2, 1998

[54] SUCCINOYLAMINO HYDROXYETHYLAMINO SULFONAMIDES USEFUL AS RETROVIRAL PROTEASE INHIBITORS

[75] Inventors: Michael L. Vazquez, Gurnee; Richard A. Mueller, Glencoe, both of Ill.; John J. Talley, St. Louis, Mo.; Daniel Getman, Chesterfield, Mo.; Gary A. DeCrescenzo, St. Peters, Mo.; John N. Freskos, Clayton, Mo.

[73] Assignees: G.D Searle & Co., Chicago, Ill.; Monsanto Company, St. Louis, Mo.

[21] Appl. No.: 541,747

[22] Filed: Oct. 10, 1995

Related U.S. Application Data

[60] Division of Ser. No. 110,912, Aug. 24, 1993, Pat. No. 5,463,104, which is a continuation-in-part of Ser. No. 935,940, Aug. 25, 1992, abandoned.

[51] Int. Cl.$^6$ ............... A61K 31/215; A61K 31/19; A61K 31/18
[52] U.S. Cl. ............... 514/539; 514/550; 514/562; 514/603; 514/604
[58] Field of Search ............... 514/533, 539, 514/555, 562, 603, 64

[56] References Cited

U.S. PATENT DOCUMENTS

| H725 | 1/1990 | Gordon | 548/533 |
|---|---|---|---|
| 4,450,164 | 5/1984 | Bristol et al. | 424/256 |
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,599,198 | 7/1986 | Hoover | 260/998.2 |
| 4,616,088 | 10/1986 | Ryono et al. | 546/336 |
| 4,668,769 | 5/1987 | Hoover | 530/331 |
| 4,668,770 | 5/1987 | Boger et al. | 530/331 |
| 4,757,050 | 7/1988 | Natarajan et al. | 514/18 |
| 4,880,938 | 11/1989 | Freidinger | 548/492 |
| 4,963,530 | 10/1990 | Hemmi et al. | 514/19 |
| 4,977,277 | 12/1990 | Rosenberg et al. | 549/215 |

FOREIGN PATENT DOCUMENTS

| 114993 | 6/1984 | European Pat. Off. | C07C 103/52 |
|---|---|---|---|
| 104041 | 8/1984 | European Pat. Off. | C07C 103/52 |
| 172347 | 2/1986 | European Pat. Off. | C07K 5/00 |
| 223437 | 5/1987 | European Pat. Off. | C07K 5/00 |
| 0 264 795 | 4/1988 | European Pat. Off. | C07K 5/00 |
| 337714 | 10/1989 | European Pat. Off. | C07K 5/02 |
| 0 342 541 | 11/1989 | European Pat. Off. | C07K 5/02 |
| 0 346 847 | 12/1989 | European Pat. Off. | C07D 207/10 |
| 356223 | 2/1990 | European Pat. Off. | C07K 37/64 |
| 389898 A2 | 10/1990 | European Pat. Off. | C07K 5/02 |
| 393445 | 10/1990 | European Pat. Off. | A61K 37/64 |
| 393457 | 10/1990 | European Pat. Off. | C07K 5/06 |
| 402646 | 12/1990 | European Pat. Off. | C07D 213/40 |
| 468641 | 1/1992 | European Pat. Off. | C07D 5/02 |
| 2184730 | 7/1987 | United Kingdom | C07K 5/00 |
| 220115 | 7/1988 | United Kingdom | C07C 103/00 |
| 2209752 | 5/1989 | United Kingdom | C07C 103/30 |
| WO84/03044 | 8/1984 | WIPO | A61K 37/64 |
| 92/08699 | 5/1992 | WIPO | C07D 215/48 |

OTHER PUBLICATIONS

Rich et al, Peptide Inhibitors of Proteases, 511–520.
Rosenberg et al, *J. Med. Chem.*, 30, 1224–1228 (1987).
Roberts et al, "Rational Design of Peptide–based Proteinase Inhibitors," *Science*, 248, 358 (1990).
Erickson et al, "Design Activity, and 2.8Å Crystal Structure of a $C_2$ Symmetric Inhibitor Complexed to HIV–1 Protease," Science, 249, 527 (1990).
Pearl et al, "Sequence specificity of retroviral proteases" *Nature*, 328, (1987).
Martin, *Drug of the Future*, 16(3), 210–212 (1991).
Meek et al, *Letter To Nature*, 343, 90–92 (1990).
McQuade et al, *Science*, 247, 454–456 (1990).
Darke, et al., "HIV Protease as an inhibitor Target for the Treatment of AIDS", Advances in Pharmacology (25), 399–453, 1994.

*Primary Examiner*—Robert Gerstl
*Attorney, Agent, or Firm*—Banner & Witcoff, Ltd.

[57] ABSTRACT

Succinoylamino hydroxyethylamino sulfonamide compounds are effective as retroviral protease inhibitors, and in particular as inhibitors of HIV protease.

20 Claims, No Drawings

SUCCINOYLAMINO HYDROXYETHYLAMINO SULFONAMIDES USEFUL AS RETROVIRAL PROTEASE INHIBITORS

RELATED APPLICATION

This is a divisional of application Ser. No. 08/110,912 filed Aug. 24, 1993, now U.S. Pat. No. 5,463,104 which is a continuation in part of application Ser. No. 07/935,490, filed Aug. 25, 1992, abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to sulfonamide-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors," *Science*, 248, 358 (1990); and Erickson et al, "Design Activity, and 2.8Å Crystal Structure of a $C_2$ Symmetric Inhibitor Complexed to HIV-1 Protease," *Science*, 249, 527 (1990).

Several classes of compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200;115, GB 2,209,752, EP 0 264,795, U.S. SIR H725 and U.S. Pat. No. 4,599,198 disclose urea-containing hydroxyethylamine renin inhibitors. G.B. 2,200,115 also disclose certain sulfamoyl-containing hydroxyethylamine renin inhibitors. EP 0 264 795 also discloses certain sulfonamide-containing renin inhibitor compounds. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as succinoylamino hydroxyethylamino sulfonamide inhibitor compounds.

DETAILED DESCRIPTION OF THE INVENTION

In accordance with the present invention, there is provided a retroviral protease inhibiting compound of the formula:

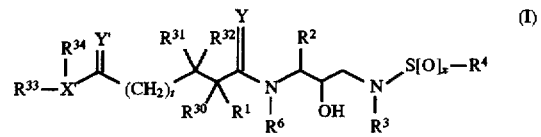

or a pharmaceutically acceptable salt, prodrug or ester thereof wherein:

x represents 0, 1 or 2;

t represents either 0 or 1;

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SH)$ —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, o-alkyl serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, and —$NO_2$, —$C{\equiv}N$, $CF_3$, —$OR^9$, —$SR^9$ wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O and $C(R^{17})$ where $R^{17}$ represents hydrogen and alkyl radicals;

Y and Y' independently represent O, S and $NR^{15}$ wherein $R^{15}$ represents hydrogen and radicals as defined for $R^3$;

R[4] represents radicals as defined by R[3] except for hydrogen;
R[6] represents hydrogen and alkyl radicals as defined for R[3];
R[30], R[31] and R[32] represent radicals as defined for R[1], or one of R[1] and R[30] together with one of R[31] and R[32] and the carbon atoms to which they are attached form a cycloalkyl radical; and R[33] and R[34] independently represent hydrogen, radicals as defined for R[3] or R[33] and R[34] together with X' represent cycloalkyl, aryl, heterocyclyl and heteroaryl radicals, provided that when X' is O; R[34] is absent.

A preferred class of retroviral inhibitor compounds of the present invention are those represented by the formula:

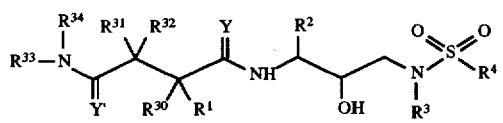

or a pharmaceutically acceptable salt, prodrug or ester thereof, preferably wherein the absolute stereochemistry about the hydroxy group is designated as (R);

R[1] represents hydrogen, —CH$_2$SO$_2$NH$_2$, —CO$_2$CH$_3$, —CONHCH$_3$, —CON(CH$_3$)$_2$, —CH$_2$C(O)NHCH$_3$, —CH$_2$C(O)N(CH$_3$)$_2$, —CONH$_2$, —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

R[2] represents alkyl, aryl, cycloalkyl, cycloalkylalkyl, and aralkyl radicals, which radicals are optionally substituted with a group selected from alkyl and halogen radicals, NO$_2$, —C≡N, CF$_3$, OR[9] and SR[9] wherein R[9] represents hydrogen and alkyl radicals;

R[3] represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl,. aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

R[4] represents radicals as defined by R[3] except for hydrogen;
R[30], R[31] and R[32] represent radicals as defined for R[1], or one of R[1] and R[30] together with one of R[31] and R[32] and the carbon atoms to which they are attached form a cycloalkyl radical; and R[33] and R[34] independently represent hydrogen, radicals as defined for R[3] or R[33] and R[34] together with the nitrogen atom to which they are attached represent heterocycloalkyl and heteroaryl radicals;

Y and Y' independently represent O, S, and NR15 wherein R[15] represents hydrogen and radicals as defined for R[3]; Preferably, Y and Y' represent O.

Yet another preferred class of compounds are those represented by the formula:

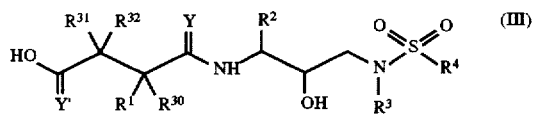

or a pharmaceutically acceptable salt, prodrug or ester thereof, preferably-wherein the stereochemistry about the hydroxy group is designated as R, wherein Y, Y', R[1], R[2], R[3], R[4], R[30], R[31] and R[32] are as defined above with respect to Formula (II). Preferably, Y and Y' represent O.

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, isoamyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, 1,4-butadienyl and the like. The term alkynyl, alone or in combination, means a straight-chain hydrocarbon radical having one or more triple bonds and containing from 2 to about 10 carbon atoms. Examples of alkynyl radicals include ethynyl, propynyl, propargyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro, cyano, haloalkyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O—aralkyl in which the term "aralkyl" has the significance given above. An example of an aralkoxycarbonyl radical is benzyloxycarbonyl. The term "aryloxy" means a radical of the formula aryl—O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl; cyclohexanecarbonyl, adamantanecarbonyl, and the like, or from a benz-fused monocyclic cycloalkanecarboxylic acid which is optionally substituted by, for example, alkanoylamino, such as 1,2,3, 4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclylalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, and the like. The term "cycloalkylalkoxycarbonyl" means an acyl group derived from a cycloalkylalkoxycarboxylic acid of the formula cycloalkylalkyl-O-COOH wherein cycloalkylalkyl has the significance given above. The term "aryloxyalkanoyl" means an acyl radical of the formula aryl-O-alkanoyl wherein aryl and alkanoyl have the significance given above. The term "heteracyclyloxycarbonyl" means an acyl group derived from heterocyclyl-O-COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O-COOH wherein heterocyclyl has the significance given above. The term "heteroaryloxycarbonyl" means an acyl radical derived from a carboxylic acid represented by heteroaryl-O-COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "leaving group" generally refers to groups readily displaceable by a nucleophile, such as an amine, a thiol or an alcohol nucleophile. Such leaving groups are well known in the art. Examples of such leaving groups include N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable, to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedure. An N-protected chloroketone derivative of an amino acid having the formula:

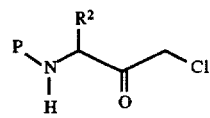

wherein P represents an amino protecting group, and $R^2$ is as defined above, is reduced to the corresponding alcohol utilizing an appropriate reducing agent. Suitable amino protecting groups are well known in the art and include carbobenzoxy, butyryl, t-butoxycarbonyl, acetyl, benzoyl and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from -10° C. to about 25° C., preferably at about 0° C., in a suitable solvent system such as, for example, tetrahydrofuran, and the like. The N-protected chloroketones are commercially available e.g. such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be used directly, as described below, or, preferably, is then reacted, preferably at room temperature, with a suitable base in a suitable solvent system to produce an N-protected amino epoxide of the formula:

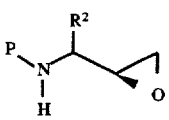

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

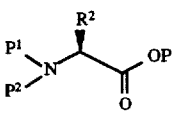

wherein $p^1$ and $p^2$ independently represent hydrogen, benzyl and amino-protecting groups as defined above with respect to P, provided that $p^1$ and p2 are not both hydrogen; $p^3$ represents a carboxyl protecting group such as methyl, ethyl, tertiary-butyl, benzyl, and the like, and $R^2$ is as defined above.

The amino-protected L-amino acid ester is then reduced, to the corresponding alcohol. For example, the amino-protected L-amino acid ester can be reduced with diisobutylaluminum hydride at −78° C. in a suitable solvent such as toluene. The resulting alcohol is then converted, for example, by way of a Swern oxidation, to the corresponding aldehyde of the formula:

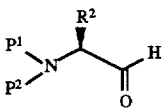

wherein $p^1$, $p^2$ and $R^2$ are as defined above. Thus, a dichloromethane solution of the alcohol is added to a cooled (−75° to −68° C.) solution of oxalyl chloride in dichloromethane and DMSO in dichloromethane and stirred for 35 minutes.

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

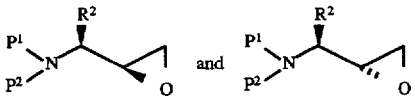

The diastereomers can be separated, e.g., by chromatography or, alternatively, once reacted in subsequent steps the diastereomeric products can be separated. For compounds having the (S) stereochemistry, a D-amino acid can be utilized in place of the L-amino acid.

The amino epoxide is then reacted, in a suitable solvent system, with an equal amount, or preferably an excess of, a desired amine of the formula:

$R^3NH_2$ wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic solvents, such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) can be represented by the formulas:

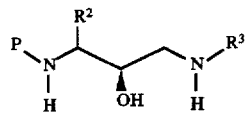

and

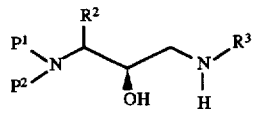

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with a sulfonyl chloride ($R^4SO_2Cl$) or sulfonyl anhydride in the presence of an acid scavenger. Suitable solvents in which the reaction can be conducted include methylene chloride, tetrahydrofuran and the like. Suitable acid scavangers include triethylamine, pyridine and the like. Preferred sulfonyl chlorides are methanesulfonyl chloride and benzenesulfonyl chloride. The resulting sulfonamide derivative can be represented, depending on the epoxide utilized by the formulas:

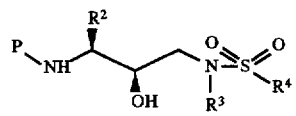

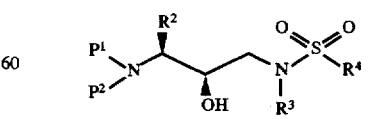

wherein P, $P^1$, $P^2$, $R^2$, $R^3$ and $R^4$ are as defined above.

The sulfonyl halides of the formula $R^4SO_2X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as PCl₅, and also to anhydrides using suitable dehydrating reagents. The sulfonic acids may in turn be prepared using procedures well known in the art. Such sulfonic acids are also commercially available.

In place of the sulfonyl halides, sulfinyl halides (R⁴SOX) or sulfenyl halides (R⁴SX) can be utilized to prepare compounds wherein the —SO₂— moiety is replaced by an —SO— or —S— moiety, respectively.

Following preparation of the sulfonamide derivative, the amino protecting group P or P¹ and P² is removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Where the protecting group is a benzyl radical, it can be removed by hydrogenolysis. Following neutralization of the salt, the amine is then reacted with a succinic acid as described below To produce the succinic acid portion of the compounds of Formula I, the starting material is a lactate of the formula:

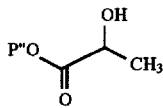

wherein P" represents alkyl and aralkyl radicals, such as, for example, ethyl, methyl, benzyl and the like. The hydroxyl group of the lactate is protected as its ketal by reaction in a suitable solvent system with methyl iso-propenyl ether (1,2-methoxypropene) in the presence of a suitable acid. Suitable solvent systems include methylene chloride, tetrahydrofuran and the like as well as mixtures thereof. Suitable acids include POCl3 and the like. It should be noted that well-known groups other than methyl isopropenyl ether can be utilized to form the ketal. The ketal is then reduced with diisobutylaluminum hydride (DIBAL) at −78° C. to produce the corresponding aldehyde which is then treated with ethylidene triphenylphosphorane (Wittig reaction) to produce a compound represented by the formula:

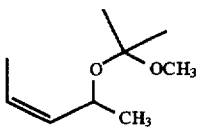

The ketal protecting group is then removed utilizing procedures well-known in the art such as by mild acid hydrolysis. The resulting compound is then esterified with isobutyryl chloride to produce a compound of the formula:

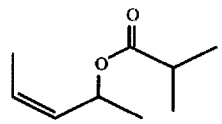

This compound is then treated with lithium diisopropyl amide at −78° C. followed by warming of the reaction mixture to room temperature to effect a Claisen rearrangement ([3,3]) to produce the corresponding acid represented by the formula:

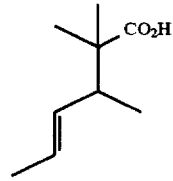

Those skilled in the art will recognize that variations on this scheme are possible, using either different protecting groups or reagents to carry out the same transformations. One can also utilize other acid chlorides in place of isobutyryl chloride to prepare similar analogs.

Treatment of the acid with benzyl bromide in the presence of a tertiary amine base, e.g., DBU, produces the corresponding ester which is then cleaved oxidatively to give a trisubstituted succinic acid:

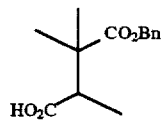

The trisubstituted succinic acid is then coupled to the sulfonamide isostere utilizing procedures well known in the art. To produce the free acid, the benzyl ester is removed by hydrogenolysis to produce the corresponding acid. The acid can then be converted to the primary amide by methods well-known in the art. The resulting product is a compound represented by Formula I.

An alternative method for preparing trisubstituted succinic acids involves reacting an ester of acetoacetic acid represented by the formula:

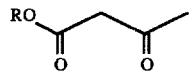

where R is a suitable protecting group, such as methyl, ethyl, benzyl or t-butyl with sodium hydride and a hydrocarbyl halide (R³¹X or R³²X) in a suitable solvent, e.g., THF, to produce the corresponding disubstituted derivative represented by the formula:

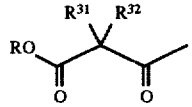

This disubstituted acetoacetic acid derivative is then treated with lithium diisopropyl amide at about −10° C. and in the presence of PhN(triflate)₂ to produce a vinyl triflate of the formula:

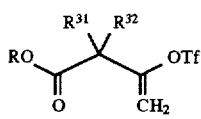

The vinyl triflate is then carbonylated utilizing a palladium catalyst, e.g., Pd(OAc)$_2$ and Ph$_3$P, in the presence of an alcohol (R"OH) or water (R"=H) and a base, e.g., triethylamine, in a suitable solvent such as DMF, to produce the olefinic ester or acid of the formula:

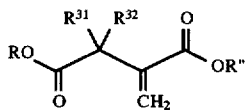

The olefin can then be subsequently asymmetrically hydrogenated, as described below, to produce a trisubstituted succinic acid derivative of the formula:

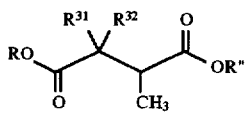

If R" is not H, R" can be removed by either hydrolysis, acidolysis, or hydrogenolysis, to afford the corresponding acid, which is then coupled to the sulfonamide isostere as described above and then, optionally, the R group removed to produce the corresponding acid, and optionally, converted to the amide.

Alternatively, one can react the sulfonamide isostere with either a suitably monoprotected succinic acid or glutaric acid of the following structure;

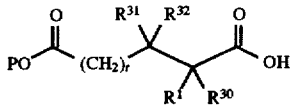

followed by removal of the protecting group and conversion of the resulting acid to an amide. One can also react an anhydride of the following structure;

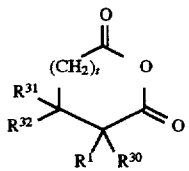

with the sulfonamide isostere and then separate any isomers or convert the resulting acid to an amide and then separate any isomers.

It is contemplated that for preparing compounds of the Formulas having R$^6$, the compounds can be prepared following the procedure set forth above and, prior to coupling the sufonamide derivative to the succinic acid portion of the molecule carried through a procedure referred to in the art as reductive amination. Thus, a sodium cyanoborohydride and an appropriate aldehyde or ketone can be reacted with the sulfonamide derivative compound or appropriate analog at room temperature in order to reductively aminate any of the compounds of Formulas I–III. It is also contemplated that where R$^3$ of the amino alcohol intermediate is hydrogen, the inhibitor compounds can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

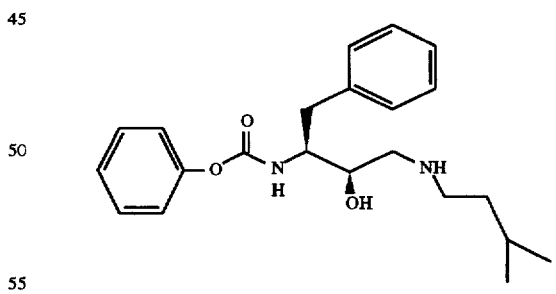

Preparation of N[3(S)-benzyloxycarbonylamino-2(R)-hydroxy-4-phenylbutyl]-N-isoamylamine

PART A:

To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li$^+$=340.

PART B:

To a solution of 6.52g (0.116 mol, 1.2 equiv.) of potassium hydroxide in 968 mL of absolute ethanol at room temperature, was added 32.3g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102°–103° C. and MH$^+$298.

Part C:

19.9 equivalents) in 90 mL of isopropyl alcohol was heated to reflux for 3.1 h. The solution was cooled to room temperature and partially concentrated in vacuo and the remaining solution poured into 200 mL of stirring hexanes whereupon the product crystallized from solution. The product was isolated by filtration and air dried to give 11.76 g, 79% of N[[3(S)-phenylmethylcarbamoyl)amino-2(R)-hydroxy-4-phenylbutyl]N-[(3-methylbutyl)]amine, mp 118°–122° C., FAB MS: MH$^+$=385.

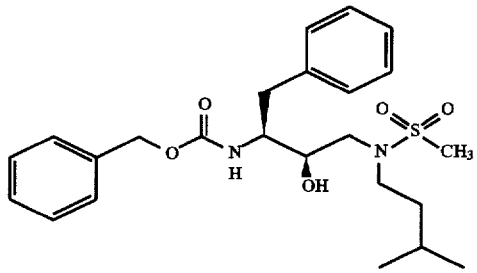

Preparation of phenylmethyl [2R-hydroxy-3-[(3-methylbutyl) (methylsulfonyl)amino]-1S-(phenylmethyl)propyl]carbamate To a solution of N[3(S)-benzyloxycarbonylamino-2(R)-hydroxy-4-phenylbutyl] N-isoamylamine from Example 1, Part C (2.0 gm, 5.2 mmol) and triethylamine (723 uL, 5.5 mmol) in dichloromethane (20 mL) was added dropwise methanesulfonyl chloride (400 uL, 5.2 mmol). The reaction mixture was stirred for 2 hours at room temperature, then the dichloromethane solution was concentrated to ca. 5 mL and applied to a silica gel column (100 gm). The column was eluted with chloroform containing 1% ethanol and 1% methanol. The phenylmethyl [2R-hydroxy-3-[(3-methylbutyl) (methylsulfonyl)amino)-1S-(phenylmethyl)propyl]carbamate was obtained as a white solid Anal. Calcd for C$_{24}$H$_{34}$N$_2$O$_5$S: C, 62.31; H, 7.41; N, 6.06. Found: C, 62.17; H, 7.55; N, 5.97.

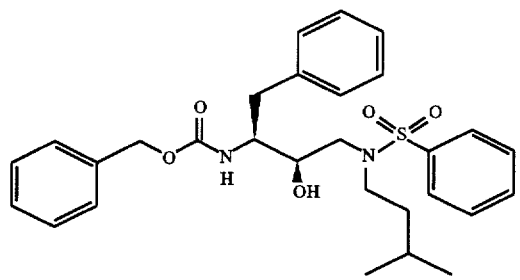

Preparation of phenylmethyl [2R-hydroxy-3-[(3-methylbutyl) (phenylsulfonyl)amino]-1S-(phenylmethyl)propyl]carbamate From the reaction of N[3(S)-benzyloxycarbonylamino-2(R)-hydroxy-4-phenylbutyl] N-isoamylamine from Example 1, Part C (1.47 gm, 3.8 mmol), triethylamine (528 uL, 3.8 mmol) and benzenesulfonyl chloride (483 uL, 3.8 mmol) one obtains phenylmethyl (2R-hydroxy-3-[(3-methylbutyl) (phenylsulfonyl)amino]-1S-(phenylmethyl)propyl]carbamate. Column chromatography on silica gel eluting with chloroform containing 1% ethanol afforded the pure product. Anal. Calcd for C$_{29}$H$_{36}$N$_2$O$_5$S: C, 66.39; H, 6.92; N, 5.34. Found: C, 66.37; H, 6.93; N, 5.26.

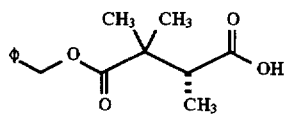

Preparation of Benzyl 2,2,3(R)-trimethylsuccinate

PART A: Preparation of Methyl (S)-lactate, 2-methoxy-2-propyl ether.

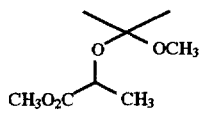

To a mixture of methyl(S)-(–s)-lactate (13.2 g, 100 mmol) and, 2-methoxypropene (21.6 g, 300 mmol) in CH$_2$Cl$_2$ (150 ml) was added POCl$_3$ (7 drops) at r.t. and the resulting mixture was stirred at this temperature for 16 hours. After the addition of Et$_3$N (10 drops), the solvents were removed in vacuo to give 20.0 g of (98%) desired product.

PART B: Preparation of 2(S)-hydroxypropanal, 2-methoxy-2-propyl ether.

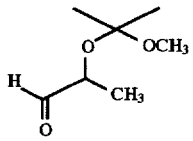

To a solution of compound from Part A (20.0 g) in CH$_2$Cl$_2$ (100 ml) was added DIBAL (65 ml of 1.5M solution in toluene, 97.5 mmol) dropwise at –78° C. for 45 min., then stirring was continued at this temperature for another 45 min. To this cold solution was added MeOH (20 ml), saturated NaCl solution (10 ml) and allowed the reaction mixture to warm up to r.t. and diluted with ether (200 ml), MgSO$_4$ (150 g) was added and stirred for another 2 h. The mixture was filtered and the solid was washed twice with ether. The combined filtrates were rotavaped to afford 11.2 g (78%) of the desired aldehyde.

PART C: Preparation of 2(S)-hydroxy-cis-3-butene, 2-methoxy-2-propyl ether.

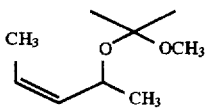

To a suspension of ethyltriphenylphosphonium bromide (28 g, 75.5 mmol) in THF (125 ml) was added KN(TMS)$_2$ (15.7 g, 95%, 75 mmol) in portions at 0° C. and stirred for 1 h at the temperature. This red reaction mixture was cooled to −78° C. and to this was added a solution of aldehyde from Part B (11 g, 75 mmol) in THF (25 ml). After the addition was completed, the resulting reaction mixture was allowed to warm up to r.t. and stirred for 16 h. To this mixture was added saturated NH$_4$Cl (7.5 ml) and filtered through a pad of celite with a thin layer of silica gel on the top. The solid was washed twice with ether. The combined filtrates were concentrated in vacuo to afford 11.5 g of crude product. The purification of crude product by flash chromatography (silica gel, 10:1 Hexanes/EtoAc) affording 8.2 g (69%) pure alkene.

PART D: Preparation of 2(S)-hydroxy-cis-3-butene.

A mixture of alkene from Part C (8.2 g) and 30% aqueous acetic acid (25 ml) was stirred at r.t. for 1 hour. To this mixture was added NaHCO$_3$ slowly until the pH was ~7, then extracted with ether (10 ml ×5). The combined ether solutions were dried (Na$_2$SO$_4$) and filtered. The filtrate was distilled to remove the ether to give 2.85 g (64%) pure alcohol, m/e=87(M+H).

PART E: Preparation of 2,2,3-trimethyl-hex-(trans)-4-enoic acid.

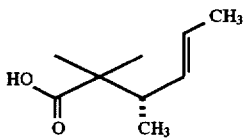

To a mixture of alcohol from Part D (2.5 g, 29 mmol) and pyridine (2.5 ml) in CH$_2$Cl$_2$ (60 ml) was added isobutyryl chloride (3.1 g, 29 mmol) slowly at 0° C. The resulting mixture was stirred at r.t. for 2 hours then washed with H$_2$O (30 ml ×2) and sat. NaCl (25 ml). The combined organic phases were dried (Na$_2$SO$_4$), concentrated to afford 4.2 g (93%) ester 2(S)-hydroxy-cis-3-butenyl isobutyrate. This ester was dissolved in THF (10 ml) and was added to a 1.0M LDA soln. (13.5 ml of 2.0M LDA solution in THF and 13.5 ml of THF) slowly at −78° C. The resulting mixture was allowed to warm up to r.t. and stirred for 2 h and diluted with 5% NaOH (40 ml). The organic phase was separated, the aqueous phase was washed with Et$_2$O (10 ml). The aqueous solution was collected and acidified with 6N HCl to pH 3. The mixture was extracted with ether (30 ml ×3). The combined ether layers were washed with sat. NaCl (25 ml), dried (Na$_2$SO$_4$) and concentrated to afford 2.5 g (60%) of desired acid, m/e=157(M+H).

PART F: Preparation of benzyl 2,2,3(S)-trimethyl-trans-4-hexenoate.

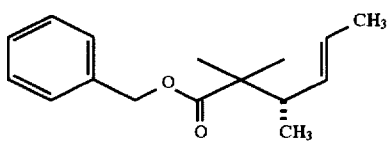

A mixture of acid from Part E (2.5 g, 16 mmol), BnBr (2.7 g, 15.8 mmol), K$_2$CO$_3$ (2.2 g, 16 mmol), NaI (2.4 g) in acetone (20 ml) was heated at 75° C. (oil bath) for 16 h. The acetone was stripped off and the residue was dissolved in H$_2$O (25 ml) and ether (35 ml). The ether layer was separated, dried (Na$_2$SO$_4$) and concentrated to afford 3.7 g (95%) of benzyl ester, m/e=247(M+H).

PART G: Preparation of benzyl 2,2,3(R)-trimethylsuccinate.

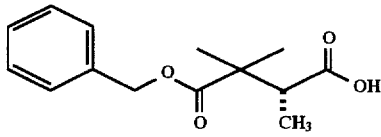

To a well-stirred mixture of KMnO$_4$ (5.4 g, 34, 2 mmol), H$_2$O (34 ml), CH$_2$Cl$_2$ (6 ml) and benzyltriethylammonium chloride (200 mg) was added a solution of ester from Part F (2.1 g, 8.54 mmol) and. acetic acid (6 ml) in CH$_2$Cl$_2$ (28 ml) slowly at 0° C. The resulting mixture was stirred at the temperature for 2 h then r.t. for 16 h. The mixture was cooled in an ice-water bath, to this was added 6N HCl (3 ml) and solid NaHSO$_3$ in portions until the red color disappeared. The clear solution was extracted with CH$_2$Cl$_2$ (30 ml ×3). The combined extracts were washed with sat. NaCl solution, dried (Na$_2$SO$_4$) and concentrated to give an oil. This oil was dissolved in Et$_2$O (50 ml) and to this was added sat. NaHCO$_3$ (50 ml). The aqueous layer was separated and acidified with 6N HCl to pH ~3 then extracted with Et$_2$O (30 ml ×3). The combined extracts were washed with sat. NaCl solution (15 ml), dried (Na$_2$SO$_4$) and concentrated to afford 725 mg (34%) of desired acid, benzyl 2,2,3(R)-trimethylsuccinate, m/e=251(M+H).

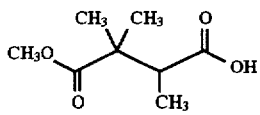

Preparation of methyl 2,2-dimethyl-3-methyl succinate, (R) and (S) isomers.

PART A: Preparation of methyl 2,2-dimethyl-3-oxo-butanoate.

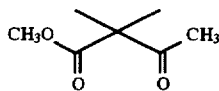

A 250 mL RB flask equipped with magnetic stir bar and N$_2$ inlet was charged with 100 ml dry THF and 4.57 g (180 mmol) of 95% NaH. The slurry was cooled to −20° C. and 10 g (87 mmol) methyl acetoacetate was added dropwise followed by 11.3 ml (181 mmol) CH$_3$I. The reaction was stirred at 0° C. for 2 hours and let cool to room temperature overnight. The reaction was filtered to remove NaI and diluted with 125 ml Et$_2$O. The organic phase was washed with 1×100 l 5% brine, dried and concentrated in vacuo to a dark golden oil that was filtered through a 30 g plug of silica gel with hexane. Concentration in vacuo yielded 10.05 g of desired methyl ester, as a pale yellow oil, suitable for use without further purification.

PART B: Preparation of methyl 2,2-dimethyl-3-0-(trifluoromethanesulfonate)-but-3-enoate.

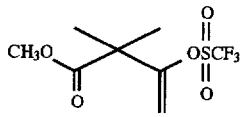

A 250 ml RB flask equipped with magnetic stir bar and $N_2$ inlet was charged with 80 mL by THF and 5.25 ml (37.5 mmol) diisopropylamine was added. The solution was cooled to −25° C. (dry ice/ethylene glycol) and 15 ml (37.5 mmol) of 2.5M n-BuLi in hexanes was added. After 10 minutes a solution of 5 g (35 mmol) 1 in 8 ml dry THF was added. The deep yellow solution was stirred at −20° C. for 10 min. then 12.4 g N-phenyl bis(trifluoromethanesulfonimide) (35 mmol) was added. The reaction was stirred @−10° C. for 2 hours, concentrated in vacuo and partioned between ethyl acetate and sat. $NaHCO_3$. The combined organic phase was washed with $NaHCO_3$, brine and conc. to an amber oil that was filtered through a 60 g silica gel plug with 300 mL 5% ethyl acetate/hexane. Conc. in vacuo yielded 9.0 g light yellow oil that was diluted with 65 ml ethyl acetate and washed with 2×50 ml 5% aq $K_2CO_3$, 1×10 mL brine, dried over $Na_2SO_4$ and conc. in vacuo to yield 7.5 g (87%) vinyl triflate, (m/e=277(M+H) suitable for use without further purification.

PART C: Preparation of methyl 2,2-dimethyl-3-carboxyl-but-3-enoate.

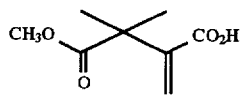

A 250 ml Fisher Porter bottle was charged with 7.5 g (27 mmol) of compound prepared in B, 50 ml dry DMF, 360 mg (1.37 mmol) triphenyl phosphine and 155 mg (0.69 mmol) Pd(II) (OAc)$_2$. The reaction mixture was purged twice with $N_2$ then charged with 30 psi CO. Meanwhile a solution of 20 ml dry DMF and 7.56 ml (54 mmol) NEt$_3$ was cooled to 0° C. to this was added 2.0 g (43 mmol) of 99% formic acid. The mixture was swirled and added to the vented Fisher Porter tube. The reaction vessel was recharged to 40 psi of CO and stirred 6 hours @ room temperature. The reaction mixture was concentrated in vacuo and partioned between 100 mL of ethyl acetate and 75 mL 5% aq $K_2CO_3$. The aqueous phase was washed with 1×40 mL additional ethyl acetate and then acidified with conc. HCl/ice. The aqueous phase was extracted with 2×70 mL of ethyl acetate and the organics were dried and conc. to yield 3.5 g (75%) white crystals, mp 72°–75° C., identified as the desired product (m/e=173 (M+H)

PART D: Preparation of methyl 2,2-dimethyl-3-methylsuccinate, isomer #1.

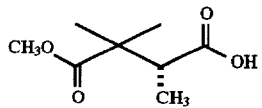

A steel hydrogenation vessel was charged with 510 mg (3.0 mmol) acrylic acid, from Part C, and 6 mg Ru (acac)$_2$ (R-BINAP) in 10 ml degassed MeOH. The reaction was hydrogenated at 50 psi/room temperature for 12 hours. The reaction was then filtered through celite and conc. to 500 mg clear oil which was shown to be a 93:7 mixture of isomer #1 and #2, respectively as determined by GC analysis using a 50M β-cyclodextrin column: 150° C. - 15 min. then ramp 2° C./min.; isomer #1, 17.85 min., isomer #2, 18–20 min.

PART E: Preparation of methyl 2,2-dimethyl-3-methylsuccinate, Isomer #2.

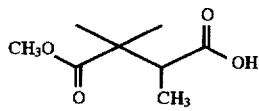

A steel hydrogenation vessel was charged with 500 mg (2.9 mmol) acrylic acid, Part C, and 6 mg Ru(OAc) (acac) (S-BINAP) in 10 ml degassed MeOH. The reaction was hydrogenated at 50 psi/room temperature for 10 hours. The reaction was filtered through celite and concentrated in vacuo to yield 490 mg of product as a 1:99 mixture of isomers #1 and #2, respectively, as determined by chiral GC as above.

In a similiar manner, one can use benzyl 2,2-dimethyl-3-oxo-butanoate to prepare benzyl 2,2,3-trimethylsuccinate, R and S isomers. Other methods for preparing succinic acids, succinates and succinamides are well known in the art and can be utilized in the present invention.

EXAMPLE 6

Preparation of Butanediamide, N$^4$-[2-hydroxy-3-[(3-methylbutyl)(phenylsulfonyl)amino]-1-(phenylmethyl)propyl]-2,2,3-Trimethyl-,[1S-[1R*(S*),2S*]]-.

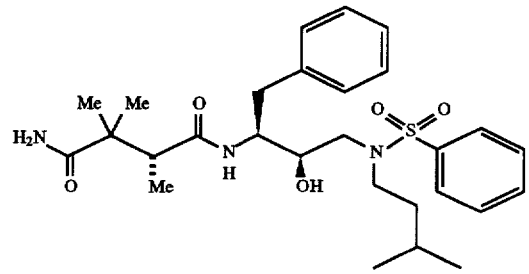

PART A:

Preparation of Butanoic acid, 4-[[2-hydroxy-3-[(3-methylbutyl)(phenylsulfonyl)amino]-1-(phenylmethyl) propyl]amino]-2,2,3-Trimethyl-4-oxo, phenylmethyl ester, [1S-[1R*(S*), 2S*]]

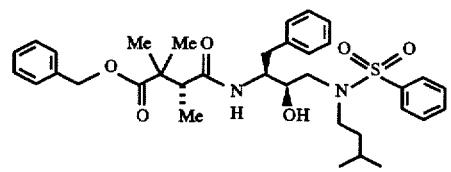

A solution of 10.1 g (19.3 mmol) of phenylmethyl[2R-hydroxy-3-[(3-methylbutyl)(phenylsulfonyl)amino]-1S-(phenylmethyl)propyl]carbamate from Example 3 in 40 mL of methanol was hydrogenated over 2 g of 10% palladium-on-carbon under 50 psig of hydrogen for six hours. After flushing with nitrogen, the catalyst was removed by filtration through celite and the filtrate concentrated to provide 7.41 g (99%) of 2(R)-hydroxy-3-[(3-methylbutyl) (phenylsulfonyl, amino]-1(S)-(phenylmethyl)propylamine.

To a solution of 2.5 g (10.0 mmol) of benzyl 2,2,3(R)-trimethylsuccinate and 2.1 g (15.0 mmol) of N-hydroxybenzotriazole in 10 mL of anhydrous N,N-dimethylformamide (DMF) at 0° C., was added 2.1 g (11.0 mmol) of 1-(3-dimethyl aminopropyl)-3-ethylcarbodiimide hydrochloride (EDC). After two hours, a solution of 3.9 g (10.0 mmol) of 2(R)-hydroxy-3-[(3-methylbutyl) (phenylsulfonyl)amino]-1S-(phenylmethyl)propylamine in 3 mL of DMF was added. After stirring at room temperature for sixteen hours, the solvent was removed under reduced pressure, the residue dissolved in ethyl acetate and then washed with 0.2N citric acid, 5% aqueous soduim bicarbonate, saturated brine, dried over anhydrous magnesuim sulfate, filtered and concentrated to afford 5.74 g of crude product. This was chromatographed over silica gel using 1% methanol/methylene chloride as eluent ($R_f$=0.08) to afford 3.87 g (62% yield) of the desired product, m/e= 533(M+H+).

PART B:

Preparation of Butanoic acid, 4-[[2-hydroxy-3-[(3-methylbutyl)(phenylsulfonyl)amino]-1-(phenylmethyl) propyl]amino]-2,2,3-trimethyl-4-oxo-(1S-[1R*(S*),2S*]]-.

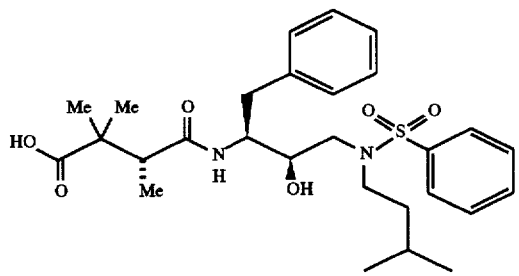

A solution of 3.87 g (6.21 mmol) of benzyl ester from part A in 40 mL of ethanol was hydrogenated over 1.5 g of 10% palladium-on-carbon under 50 psig of hydrogen for four hours. After flushing with nitrogen, the catalyst was rermoved by filtration through celite and the filtrate concentrated under reduced pressure to afford 3.24 g (98%) of desired product.

PART C:

Preparation of Butanediamide, $N^4$-[2-hydroxy-3-[(3-methylbutyl)(phenylsulfonyl)amine]-1-(phenylmethyl) propyl]-2,2,3-trimethyl-,[1S-[1R*(S*),2S*]]-.

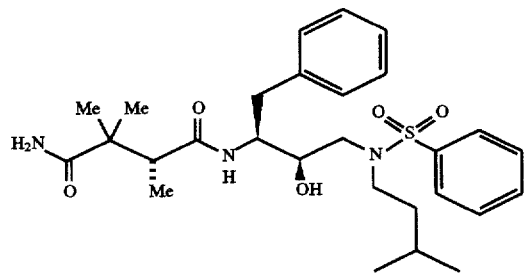

To a solution of 3.24 g (6.1 mmol) of acid from part B and 1.86 g (12.2 mmol) of N-hydroxybenzotriazole in 6 mL of anhydrous DMF at 0° C. was added 1.75 g (9.1 mmol) of EDC. After stirring at 0° C. for two hours, 3.44 g (60.8 mmol) of 30% aqueous ammonia was added. After stirring at room temperature for twenty hours, the solvents were removed under reduced pressure, the residue dissolved in ethyl acetate and then washed with 0.2N citric acid, 5% aqueous sodium bicarbonate, saturated brine, dried over anhydrous magnesium sulfate, filtered and concentrated to afford 3.75 g of crude material. This was passed through a column of 150 g of basic alumina with 20:1 (v:v) methylene chloride/methanol to remove unreacted acid. The resulting product was precipitated from methylene chloride with hexane to afford 2.1 g (65%) of the desired product, m.p. 110°–112° C., m/e=538 (m+Li).

EXAMPLE 7

In a manner analogous to that of the previous examples, the compounds listed in Table 1 were prepared.

TABLE 1

| | | | Mass Determination | |
| --- | --- | --- | --- | --- |
| Entry | COMPOUND | Formula | Calcd | Found |
| 1 | | $C_{35}H_{46}O_6N_2S$ | 623(M + H) | 623 |

TABLE 1-continued

| Entry | COMPOUND | Mass Determination | | |
|---|---|---|---|---|
| | | Formula | Calcd | Found |
| 2 | | $C_{28}H_{40}O_6N_2S$ | 539(M + Li) | 539 |
| 3 | | $C_{28}H_{41}O_5N_3S$ | 538(M + Li) | 538 |
| 4 | | $C_{34}H_{44}O_6N_2S$ | 615(M + Li) | 615 |
| 5 | | $C_{27}H_{38}O_6N_2S$ | 525(M + Li) | 525 |

TABLE 1-continued

| Entry | COMPOUND | Mass Determination Formula | Calcd | Found |
|---|---|---|---|---|
| 6 | | $C_{27}H_{39}O_5N_3S$ | 524(M + Li) | 524 |
| 7 | | $C_{35}H_{46}O_7N_2S$ | 645(M + Li) | 645 |
| 8 | | $C_{28}H_{40}O_7N_2S$ | 549(M + H) | 549 |
| 9 | | $C_{28}H_{41}O_6N_3S$ | 548(M + H) | 548 |

EXAMPLE 8

Additional exemplary compounds of the present invention are listed in Tables 2–7. These compounds could be prepared in a manner analogous to the above Examples and according to the following general procedures.

General Procedure for the Synthesis of Amino Epoxide

PART A:

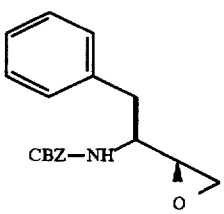

To a solution of 0.226 mol of N-benzyloxycarbonyl-L-phenylalanine chloromethyl ketone in a mixture of 807 mL of methanol and 807 mL of tetrahydrofuran at −2° C., is added 1.54 equiv. of solid sodium borohydride over one hundred minutes. The solvents are then removed under reduced pressure at 40° C. and the residue is dissolved in ethyl acetate (approx. 1L). The solution is washed sequentially with 1M potassium hydrogen sulfate, saturated sodium bicarbonate and is then saturated sodium chloride solutions. After drying over anhydrous magnesium sulfate and filtering, the solution is removed under reduced pressure. To the resulting oil is added hexane (approx. 1L) and the mixture is warmed to 60° C. with swirling. After cooling to room temperature, the solids are collected and washed with 2L of hexane. The resulting solid is recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li$^+$=340.

PART B:

To a solution of 1.2 equiv. of potassium hydroxide in 968 mL of absolute ethanol at room temperature, is added 0.097 mol of N-CBZ-3(S)-amino-1-chloro-4-phenyl-2(S)-butanol. After stirring for fifteen minutes, the solvent is removed under reduced pressure and the solids are dissolved in methylene chloride. After washing with water, drying over magnesium sulfate, filtering and stripping, one obtains a white solid. Recrystallization from hot ethyl acetate and hexane will afford N-benzyloxycarbonyl-3(S)-amino-1,2 (S) -epoxy-4-phenylbutane.

Alternate General Procedure for the Synthesis of Amino Epoxides

Step A:

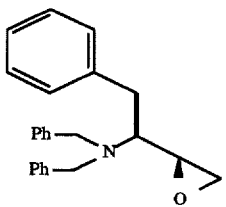

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B:

The crude benzylated product of the above step is dissolved in toluene (750 ml) and cooled to −55° C. A 1.5M solution of DIBAL-H in toluene (443.9 ml, 0.666 mol) is then added at a rate to maintain the temperature between −55° to −50° C. (addition time - 1 hour). The mixture is stirred for 20 minutes at −55° C. The reaction is quenched at −55° C. by the slow addition of methanol (37 ml). The cold solution is then poured into cold (5° C.) 1.5N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of material can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is created with ethyl acetate and hexane which provides an additional 7 g (~7% yield) of slightly impure solid product. Further optimization in the recovery from the mother liquor is probable.

Step C:

A solution of oxalyl chloride (8.4 ml, 0.096 mol) in dichloromethane (240 ml) is cooled to −74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min. followed by addition of a solution of the alcohol (0.074 mol) in 100 ml of dichloromethane (addition time −20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to −78° C. A 1.6M solution of n-butyllithium in hexane (25 ml, 0.040 mol) is then added at a rate to maintain the temperature at −75° C. (addition time - 15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product could be used in the next step without purification. The desired diastereomer can be purified by recrystallization at the subsequent sulfonamide formation step.

Alternately, the product could be purified by chromatography.

General Procedure for the Synthesis of 1,3-Diamino 4-phenyl Butan-2-ol Derivatives.

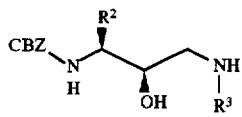

A mixture of the amine $R^3NH_2$ (20 equiv.) in dry isopropyl alcohol (20 mL/mmol of epoxide to be converted) is heated to reflux and then is treated with an N-Cbz amino epoxide of the formula:

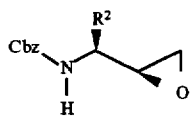

from a solids addition funnel over a 10–15 minute period. After the addition is complete the solution is maintained at reflux for an additional 15 minutes and the progress of the reaction monitored by TLC. The reaction mixture is then concentrated in vacuo to give an oil and is then treated with n-hexane with rapid stirring whereupon the ring opened-material precipitates from solution. Precipitation is generally complete within 1 hr and the product is then isolated by filtration on a Büchner funnel and is then air dried. The product is further dried in vacuo. This method affords amino alcohols of sufficient purity for most purposes.

General procedure for the Reaction of Amino Alcohols with Sulfonyl Halides or Sulfonyl Anhydrides: Preparation of Sulfonamides

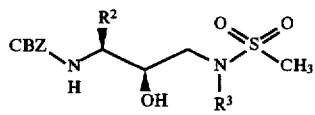

To a solution of N[3(S)-benzyloxycarbonylamino-2(R)-hydroxy-4-phenylbutyl] N-isoamylamine (2.0 gm, 5.2 mmol) and triethylamine (723 uL, 5.5 mmol) in dichloromethane (20 mL) is added dropwise methanesulfonyl chloride (400 uL, 5.2 mmol). The reaction mixture is stirred for 2 hours at room temperature, then the dichloromethane solution is concentrated to ca. 5 mL and applied to a silica gel column (100 gm). The column is eluted with chloroform containing 1% ethanol and 1% methanol.

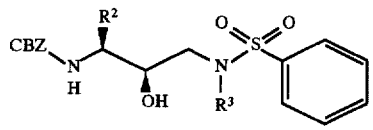

Alternatively, from the reaction of N[3(S)-benzyloxycarbonylamino-2(R)-hydroxy-4-phenylbutyl] N-isoamylamine (1.47 gm, 3.8 mmol), triethylamine (528 uL, 3.8 mmol) and benzenesulfonyl chloride (483 uL, 3.8 mmol) one can obtain the appropriate (phenylsulfonyl) amino derivative.

General Procedure for the Removal of the Protecting Groups by Hydrogenolysis with Palladium on Carbon A. Alcohol Solvent The Cbz-protected peptide derivative is dissolved in methanol (ca.20 mL/mmol) and 10% palladium on carbon catalyst is added under a nitrogen atmosphere. The reaction vessel is sealed and flushed 5 times with nitrogen and then 5 times with hydrogen. The pressure is maintained at 50 psig for 1–16 hours and then the hydrogen is replaced with nitrogen and the solution is filtered through a pad of celite to remove the catalyst. The solvent is removed in vacuo to give the free amino derivative of suitable purity to be taken directly on to the next step.

B. Acetic Acid Solvent

The Cbz-protected peptide derivative is dissolved in glacial acetic acid (20 mL/mmol) and 10% palladium on carbon catalyst is added under a nitrogen atmosphere. The reaction vessel is flushed 5 times with nitrogen and 5 times with hydrogen and then maintained at 40 psig for about 2h. The hydrogen is then replaced with nitrogen and the reaction mixture filtered through a pad of celite to remove the catalyst. The filtrate is concentrated and the resulting product is taken up in anhydrous ether and is evaporated to dryness 3 times. The final product, the acetate salt, is dried in vacuo and is of suitable purity for subsequent conversion.

General Procedure for Removal of Boc-protecting Group with 4N Hydrochloric Acid in Dioxane The Boc-protected amino acid or peptide is treated with a solution of 4N HCl in dioxane with stirring at room temperature. Generally the deprotection reaction is complete within 15 minutes, the progress of the reaction is monitored by thin layer chromatography (TLC). Upon completion, the excess dioxane and HCl are removed by evaporation in vacuo. The last traces of dioxane and HCl are best removed by evaporation again from anhydrous ether or acetone. The hydrochloride salt thus obtained is thoroughly dried in vacuo and is suitable for further reaction.

TABLE 2

[Structure: R-C(=O)-C(CH₃)₂-CH(CH₃)-C(=O)-NH-CH(CH₂Ph)-CH(OH)-CH₂-N(R³)-S(=O)₂-R⁴]

| Entry | R | R³ | R⁴ |
|---|---|---|---|
| 1 | OH | CH₃ | C₆H₅ |
| 2 | OH | i-Butyl | CH₃ |
| 3 | OH | i-Butyl | n-Butyl |
| 4 | NH₂ | i-Butyl | n-Butyl |
| 5 | OH | i-Propyl | n-Butyl |
| 6 | NH₂ | i-Propyl | n-Butyl |
| 7 | OH | C₆H₅ | n-Butyl |
| 8 | OH | —CH₂-cyclohexyl | n-Butyl |
| 9 | OH | —CH₂-phenyl | n-Butyl |
| 10 | NH₂ | —CH₂-phenyl | n-Butyl |
| 11 | OH | cyclohexyl | n-Butyl |
| 12 | OH | i-Butyl | n-Propyl |
| 13 | OH | i-Butyl | —CH₂CH(CH₃)₂ |
| 14 | OH | (R)—CH(CH₃)-phenyl | n-Butyl |
| 15 | OH | —CH₂-cyclohexyl | i-Propyl |
| 16 | OH | —CH₂-cyclohexyl | —CH₂CH₂CH(CH₃)₂ |
| 17 | OH | i-Butyl | —CH₂CH₃ |
| 18 | OH | i-Butyl | —CH(CH₃)₂ |
| 19 | OH | i-Butyl | cyclohexyl |
| 20 | NH₂ | i-Butyl | cyclohexyl |
| 21 | OH | —CH₂-cyclohexyl | —(CH₂)₂CH(CH₃)₂ |

TABLE 2-continued

| Entry | R | R³ | R⁴ |
|---|---|---|---|
| 22 | OH | (CH₂)₂CH(CH₃)₂ | —CH(CH₃)₂ |
| 23 | NH₂ | i-Butyl | —CH(CH₃)₂ |
| 24 | OH | i-Butyl | —C(CH₃)₃ |
| 25 | NH₂ | i-Butyl | —C(CH₃)₃ |
| 26 | OH | —CH₂-(2-naphthyl) | —C(CH₃)₃ |
| 27 | NH₂ | —CH₂-(2-naphthyl) | —C(CH₃)₃ |
| 28 | OH | —(CH₂)₂CH(CH₃)₂ | —C(CH₃)₃ |
| 29 | NH₂ | —(CH₂)₂CH(CH₃)₂ | —C(CH₃)₃ |
| 30 | OH | —CH₂C₆H₅ | —C(CH₃)₃ |
| 31 | NH₂ | —CH₂C₆H₅ | —C(CH₃)₃ |
| 32 | OH | —(CH₂)₂C₆H₅ | —C(CH₃)₃ |
| 33 | NH₂ | —(CH₂)₂C₆H₅ | —C(CH₃)₃ |
| 34 | OH | n-Butyl | —C(CH₃)₃ |
| 35 | OH | n-Pentyl | —C(CH₃)₃ |
| 36 | OH | n-Hexyl | —C(CH₃)₃ |
| 37 | OH | —CH₂C₆H₅ | —C(CH₃)₃ |
| 38 | OH | —CH₂C(CH₃)₃ | —C(CH₃)₃ |
| 39 | NH₂ | —CH₂C(CH₃)₃ | —C(CH₃)₃ |
| 40 | OH | —CH₂CH₂-morpholino | —C(CH₃)₃ |
| 41 | OH | —CH₂C₆H₅OCH₃(para) | —C(CH₃)₃ |
| 42 | OH | —CH₂-(3-pyridyl) | —C(CH₃)₃ |
| 43 | OH | —CH₂-(4-pyridyl) | —C(CH₃)₃ |
| 44 | OH | —(CH₂)₂C(CH₃)₃ | —C(CH₃)₃ |
| 45 | NH₂ | —(CH₂)₂C(CH₃)₃ | —C(CH₃)₃ |
| 46 | OH | —(CH₂)₄OH | —C(CH₃)₃ |
| 47 | NH₂ | —(CH₂)₄OH | —C(CH₃)₃ |
| 48 | NH₂ | —CH₂-(4-fluorophenyl) | —C(CH₃)₃ |
| 49 | NH₂ | —CH₂-(4-pyridyl) | —C(CH₃)₃ |

TABLE 2-continued

| Entry | R | R³ | R⁴ |
|---|---|---|---|
| 50 | OCH₂Ph | cyclohexyl | —C₆H₅ |
| 51 | OH | cyclohexyl | —C₆H₅ |
| 52 | NH₂ | cyclohexyl | —C₆H₅ |
| 53 | OCH₂Ph | —CH₂C₆H₁₁ | —C₆H₅ |
| 54 | OH | —CH₂C₆H₁₁ | —C₆H₅ |
| 55 | NH₂ | —CH₂C₆H₁₁ | —C₆H₅ |
| 56 | OCH₂Ph | —CH₂Ph | —C₆H₅ |
| 57 | OH | —CH₂Ph | —C₆H₅ |
| 58 | NH₂ | —CH₂Ph | —C₆H₅ |
| 59 | OCH₂Ph | —CH₂CH₂—N(morpholino) | —C₆H₅ |
| 60 | OH | —CH₂CH₂—N(morpholino) | —C₆H₅ |
| 61 | NH₂ | —CH₂CH₂—N(morpholino) | —C₆H₅ |
| 62 | OCH₂Ph | —CH₂-(4-pyridyl) | —C₆H₅ |
| 63 | OH | —CH₂-(4-pyridyl) | —C₆H₅ |
| 64 | NH₂ | —CH₂-(4-pyridyl) | —C₆H₅ |
| 65 | OCH₂Ph | —CH₂CH(CH₃)₂ | —CH₃ |
| 66 | OH | —CH₂CH(CH₃)₂ | —CH₃ |
| 67 | NH₂ | —CH₂CH(CH₃)₂ | —CH₃ |
| 68 | OCH₂Ph | —CH₂CH(CH₃)₂ | —C₆H₁₁ |
| 69 | OH | —CH₂CH(CH₃)₂ | —C₆H₁₁ |
| 70 | NH₂ | —CH₂CH(CH₃)₂ | —C₆H₁₁ |
| 71 | OCH₂Ph | —CH₂CH(CH₃)₂ | thienyl |

TABLE 2-continued

| Entry | R | R³ | R⁴ |
|---|---|---|---|
| 72 | OH | —CH₂CH(CH₃)₂ | 2-thienyl |
| 73 | NH₂ | —CH₂CH(CH₃)₂ | 2-thienyl |
| 74 | OCH₂Ph | —CH₂CH(CH₃)₂ | —CF₃ |
| 75 | OH | —CH₂CH(CH₃)₂ | —CF₃ |
| 76 | NH₂ | —CH₂CH(CH₃)₂ | —CF₃ |
| 77 | OCH₂Ph | —CH₂CH(CH₃)₂ | 4-OCH₃-C₆H₄ |
| 78 | OH | —CH₂CH(CH₃)₂ | 4-OCH₃-C₆H₄ |
| 79 | NH₂ | —CH₂CH(CH₃)₂ | 4-OCH₃-C₆H₄ |
| 80 | OCH₂Ph | —CH₂CH(CH₃)₂ | 4-F-C₆H₄ |
| 81 | OH | —CH₂CH(CH₃)₂ | 4-F-C₆H₄ |
| 82 | NH₂ | —CH₂CH(CH₃)₂ | 4-F-C₆H₄ |
| 83 | OCH₂Ph | —CH₂CH(CH₃)₂ | 4-NH₂-C₆H₄ |
| 84 | OH | —CH₂CH(CH₃)₂ | 4-NH₂-C₆H₄ |
| 85 | NH₂ | —CH₂CH(CH₃)₂ | 4-NH₂-C₆H₄ |

TABLE 3

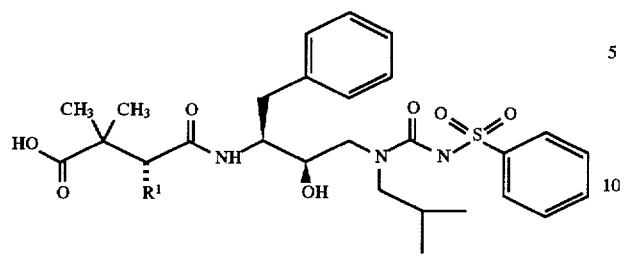

| Entry | R¹ |
|---|---|
| 1 | $CH_2SO_2CH_3$ |
| 2 | (R)—CH(OH)CH₃ |
| 3 | CH(CH₃)₂ |
| 4 | (R,S)CH₂SOCH₃ |
| 5 | $CH_2SO_2NH_2$ |
| 6 | CH₂SCH₃ |
| 7 | CH₂CH(CH₃)₂ |
| 8 | CH₂CH₂C(O)NH₂ |
| 9 | (S)—CH(OH)CH₃ |
| 10 | —CH₂C≡CH |
| 11 | —CH₂CH₃ |
| 12 | —CH₂C(O)NH₂ |

TABLE 4

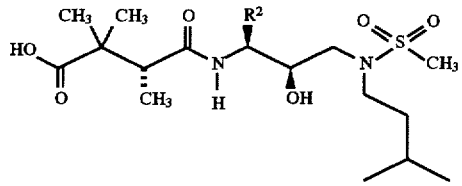

| Entry | R² |
|---|---|
| 1 | n-Bu |
| 2 | cyclohexylmethyl |
| 3 | C₆H₅CH₂ |
| 4 | 2-naphthylmethyl |
| 5 | p-F(C₆H₄)CH₂ |
| 6 | p-(PhCH₂O)(C₆H₄)CH₂ |
| 7 | p-HO(C₆H₄)CH₂ |

TABLE 5

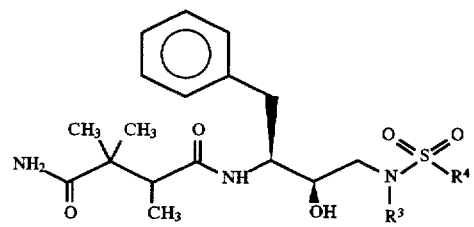

| Entry | R³ | R⁴ |
|---|---|---|
| 1 | —CH₂CH(CH₃)₂ | —CH(CH₃)₂ |
| 2 | —CH₂CH(CH₃)₂ | 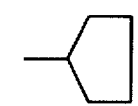 |
| 3 | —CH₂CH(CH₃)₂ | (cyclobutyl) |
| 4 | —CH₂CH(CH₃)₂ | (cyclopentyl) |
| 5 | —CH₂CH(CH₃)₂ | 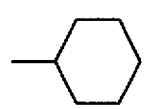 |

TABLE 6

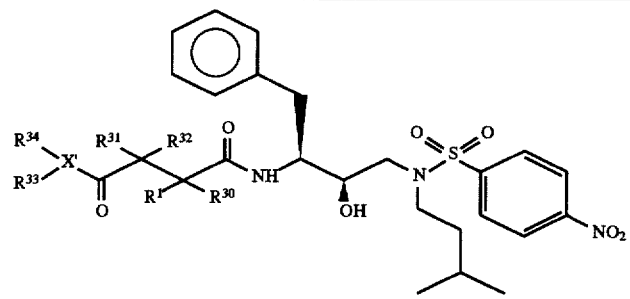

| Entry | R¹ | R³⁰ | R³¹ | R³² | X' | R³³ | R³⁴ |
|---|---|---|---|---|---|---|---|
| 1 | H | H | H | H | N | H | H |
| 2 | H | H | H | H | O | H | — |
| 3 | H | H | H | H | O | CH₃ | — |

TABLE 6-continued

| Entry | R¹ | R³⁰ | R³¹ | R³² | X' | R³³ | R³⁴ |
|---|---|---|---|---|---|---|---|
| 4 | CH₃ | H | H | H | N | H | H |
| 5 | CH₃ | H | H | H | O | H | — |
| 6 | H | H | CH₃ | H | N | H | H |
| 7 | H | H | CH₃ | H | O | H | — |
| 8 | CH₃ | CH₃ | H | H | N | H | H |
| 9 | CH₃ | CH₃ | H | H | O | H | — |
| 10 | CH₃ | CH₃ | H | H | O | CH₂C₆H₄OCH₃ | — |
| 11 | H | H | CH₃ | CH₃ | N | H | H |
| 12 | H | H | CH₃ | CH₃ | O | H | — |
| 13 | H | H | CH₃ | CH₃ | O | CH₂C₆H₄OCH₃ | — |
| 14 | CH₃ | H | CH₃ | H | N | H | H |
| 15 | CH₃ | H | CH₃ | H | N | H | CH₃ |
| 16 | CH₃ | H | CH₃ | H | N | CH₃ | CH₃ |
| 17 | CH₃ | H | CH₃ | H | O | H | — |
| 18 | CH₃ | H | CH₃ | H | O | —CH₂C₆H₅OCH₃ | — |
| 19 | OH | H | H | H | N | H | H |
| 20 | OH | H | H | H | O | H | — |
| 21 | H | H | OH | H | N | H | H |
| 22 | H | H | OH | H | O | H | — |
| 23 | CH₂ | H | H | H | N | H | H |
| 24 | CH₂C(O)NH₂ | H | H | H | N | H | H |
| 25 | CH₂C(O)NH₂ | H | H | H | O | H | — |
| 26 | CH₂C(O)NH₂ | H | H | H | O | CH₃ | — |
| 27 | CH₂Ph | H | H | H | N | H | H |
| 28 | CH₃ | H | CH₃ | CH₃ | O | CH₂Ph | — |
| 29 | CH₃ | H | CH₃ | CH₃ | O | H | — |
| 30 | CH₃ | H | CH₃ | CH₃ | N | H | H |
| 31 | CH₃ | H | CH₃ | CH₃ | N | H | CH₃ |
| 32 | CH₃ | H | CH₃ | CH₃ | N | CH₃ | CH₃ |
| 33 | CH₂CH₃ | H | CH₃ | CH₃ | O | H | — |
| 34 | CH₂CH₃ | H | CH₃ | CH₃ | N | H | H |
| 35 | CH₃ | H | CH₂CH₃ | CH₂CH₃ | O | H | — |
| 36 | CH₃ | H | CH₂CH₃ | CH₂CH₃ | N | H | H |

TABLE 7

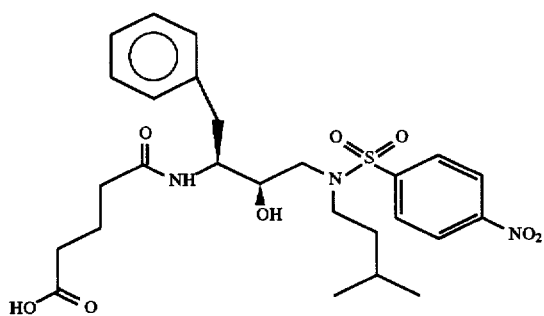

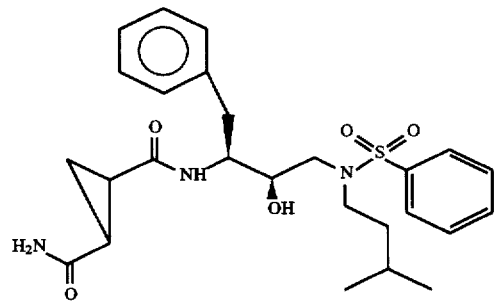

TABLE 7-continued

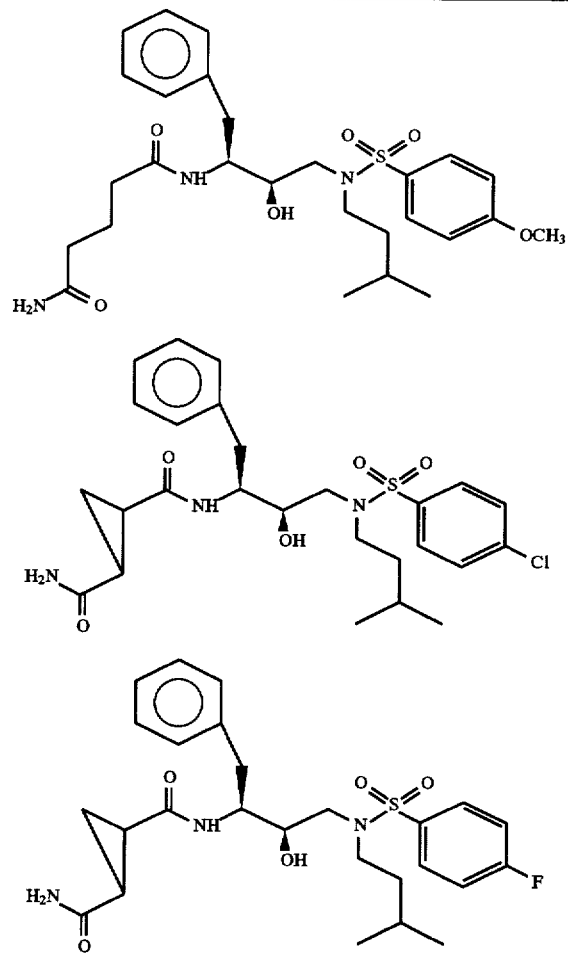

EXAMPLE 9

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 8. The enzyme method is described below. The substrate is 2-aminobenzoyl-Ile-Nle-Phe(p-$NO_2$)-Gln-Arg$NH_2$. The positive control is MVT-101 (Miller, M. et al, Science, 246, 1149 (1989)] The assay conditions are as follows:

Assay buffer:

20 mM sodium phosphate, pH 6.4
20% glycerol
1 mM EDTA
1 mM DTT
0.1% CHAPS

The above described substrate is dissolved in DMSO, then diluted 10 fold in assay buffer. Final substrate concentration in the assay is 80 μM.

HIV protease is diluted in the assay buffer to a final enzyme concentration. of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

TABLE 8

| Entry | Compound | $IC_{50}$ (nM) |
|---|---|---|
| 1 | | 80 |

TABLE 8-continued

| Entry | Compound | IC$_{50}$ (nM) |
|-------|----------|----------------|
| 2 | | 2 |
| 3 | | 2 |
| 4 | | 34 |
| 5 | | 1 |

TABLE 8-continued

| Entry | Compound | IC$_{50}$ (nM) |
|---|---|---|
| 6 | (structure) | 2 |
| 7 | (structure) | 16 |
| 8 | (structure) | 2 |
| 9 | (structure) | 2 |

EXAMPLE 10

The effectiveness of the compounds listed in Table 8 were determined in the above-described enzyme assay and in a CEM cell assay.

The HIV inhibition assay method of acutely infected cells is an automated tetrazolium based s calorimetric assay essentially that reported by Pauwles et al, *J. Virol. Methods* 20, 309–321 (1988). Assays were performed in 96-well tissue culture plates. CEM cells, a CD4$^+$ cell line, were grown in RPMI-1640 medium (Gibco) supplemented with a 10% fetal calf serum and were then treated with polybrene (2 μg/ml). An 80 μl volume of medium containing 1×10$^4$ cells was dispensed into each well of the tissue culture plate. To each well was added a 100 μl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 μL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|   | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% $CO_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazolium bromide (MTT) was added to each 100 µL cell suspension, and the cells were incubated for 4 hours at 27° C. in a 5% $CO_2$ environment. During this incubation, MTT is metabolically reduced by living cells resulting in the production in the cell of a colored formazan product. To each sample was added 100 µl of 10% sodium dodecylsulfate in 0.01N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 9

| Entry | Compound | $IC_{50}$ (nm) | $EC_{50}$(nm) | $TD_{50}$(nm) |
|---|---|---|---|---|
| 1 | | 2 | 15 | |
| 2 | | 2 | 9 | 60,000 |
| 3 | | 1 | 42 | 220,000 |

TABLE 9-continued

| Entry | Compound | IC$_{50}$ (nm) | EC$_{50}$(nm) | TD$_{50}$(nm) |
|---|---|---|---|---|
| 4 | (structure) | 2 | 5 | 62,000 |
| 5 | (structure) | 2 | 27 | 200,000 |
| 6 | (structure) | 2 | 5 | 58,000 |

Utilizing the procedures set forth above in the examples along with the general description, it is contemplated that the compounds listed below could be prepared and that such compounds would have activities as HIV protease inhibitors substantially similar to the activities of the compounds set forth in the examples.

The compounds of the present invention are effective antiviral compounds and, in particular, are effective retroviral inhibitors as shown above. Thus, the subject compounds are effective HIV protease inhibitors. It is contemplated that the subject compounds will also inhibit other strains of HIV such as HIV-2, and other viruses such as human T-cell leukemia virus, simian immunodeficiency virus, feline leukemia virus, respiratory syncitial virus, hepadnavirus, cytomegalovirus and picornavirus. Thus, the subject compounds are effective in the treatment and/or proplylaxis of retroviral infections.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT or with N-butyl-1-deoxynojirimycin for the prophylasis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Method of inhibiting a retroviral protease comprising administering a protease inhibiting amount of a composition comprising (1) a compound of the following formula, or a pharmaceutically acceptable salt or ester thereof, and (2) a pharmaceutically acceptable carrier:

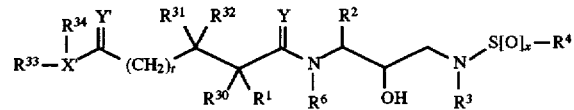

wherein:

x represents 0, 1 or 2;

t represents either 0 or 1;

$R^1$ represents hydrogen, $-CH_2SO_2NH_2$, $-CO_2CH_3$, $-CONHCH_3$, $-CON(CH_3)_2$, $-CH_2C(O)NHCH_3$, —CH$_2$C(O)N(CH$_3$)$_2$, —CONH$_2$, —C(CH$_3$)$_2$(SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, o-alkyl serine, aspartic acid, beta-cyano alanine, and allothreonine side chains;

R$^2$ represents alkyl, aryl, cycloalkyl, cycloalkylalkyl and aralkyl radicals, which radicals are optionally substituted with a group selected from halogen and alkyl radicals, —NO$_2$, —C≡N, CF$_3$, —OR$^9$ and —SR$^9$, wherein R$^9$ represents hydrogen and alkyl radicals;

R$^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and C(R$^{17}$) wherein R$^{17}$ represents hydrogen and alkyl radicals;

Y and Y' independently represent O, S and NR$^{15}$ wherein R$^{15}$ represents hydrogen and radicals as defined for R$^3$;

R$^4$ represents radicals as defined by R$^3$ except for hydrogen;

R$^6$ represents hydrogen and alkyl radicals;

R$^{30}$, R$^{31}$ and R$^{32}$ represent radicals as defined for R$^1$, or one of R$^1$ and R$^{30}$ together with one of R$^{31}$ and R$^{32}$ and the carbon atoms to which they are attached form a cycloalkyl radical; or R$^{30}$ and R$^{32}$ together with the carbon atoms to which they are attached form a three to six-membered cycloalkyl radical; and R$^{33}$ and R$^{34}$ independently represent hydrogen, radicals as defined for R$^3$, or R$^{33}$ and R$^{34}$ together with X' represent cycloalkyl, aryl, heterocyclyl and heteroaryl radicals, provided that when X' is O, R$^{34}$ is absent.

2. Method of treating a retroviral infection comprising administering an effective amount of a composition comprising (1) a compound of the following formula, or a pharmaceutically acceptable salt or ester thereof, and (2) a pharmaceutically acceptable carrier:

$$R^{33}-X' \overset{R^{34}}{\underset{|}{\phantom{X}}} \overset{Y'}{\underset{\|}{C}} (CH_2)_t \overset{R^{31}}{\underset{R^{30}}{\phantom{C}}} \overset{R^{32}}{\underset{R^{1}}{C}} \overset{Y}{\underset{\|}{C}} \overset{R^{2}}{\underset{R^{6}}{N}} \overset{}{\underset{OH}{CH}} \overset{}{\underset{R^{3}}{N}} S[O]_x-R^4$$

wherein:

x represents 0, 1 or 2;

t represents either 0 or 1;

R$^1$ represents hydrogen, —CH$_2$SO$_2$NH$_2$, —CO$_2$CH$_3$, —CONHCH$_3$, —CON(CH$_3$)$_2$, —CH$_2$C(O)NHCH$_3$, —CH$_2$C(O)N(CH$_3$)$_2$, —CONH$_2$, —C(CH$_3$)$_2$(SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, o-alkyl serine, aspartic acid, beta-cyano alanine, and allothreonine side chains;

R$^2$ represents alkyl, aryl, cycloalkyl, cycloalkylalkyl and aralkyl radicals, which radicals are optionally substituted with a group selected from halogen and alkyl radicals, —NO$_2$, —C≡N, CF$_3$, —OR$^9$ and —SR$^9$, wherein R$^9$ represents hydrogen and alkyl radicals;

R$^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and C(R$^{17}$) wherein R$^{17}$ represents hydrogen and alkyl radicals;

Y and Y' independently represent O,S and NR$^{15}$ wherein R$^{15}$ represents hydrogen and radicals as defined for R$^3$;

R$^4$ represents radicals as defined by R$^3$ except for hydrogen;

R$^6$ represents hydrogen and alkyl radicals;

R$^{30}$, R$^{31}$ and R$^{32}$ represent radicals as defined for R$^1$, or one of R$^1$ and R$^{30}$ together with one of R$^{31}$ and R$^{32}$ and the carbon atoms to which they are attached form a cycloalkyl radical; or R$^{30}$ and R$^{32}$ together with the carbon atoms to which they are attached form a three to six-membered cycloalkyl radical; and R$^{33}$ and R$^{34}$ independently represent hydrogen, radicals as defined for R$^3$, or R$^{33}$ and R$^{34}$ together with X' represent cycloalkyl, aryl, heterocyclyl and heteroaryl radicals, provided that when X' is O, R$^{34}$ is absent.

3. Method for treating AIDS comprising administering an effective amount of a composition comprising (1) a compound of the following formula, or a pharmaceutically acceptable salt or ester thereof, and (2) a pharmaceutically acceptable carrier:

$$R^{33}-X' \overset{R^{34}}{\underset{|}{\phantom{X}}} \overset{Y'}{\underset{\|}{C}} (CH_2)_t \overset{R^{31}}{\underset{R^{30}}{\phantom{C}}} \overset{R^{32}}{\underset{R^{1}}{C}} \overset{Y}{\underset{\|}{C}} \overset{R^{2}}{\underset{R^{6}}{N}} \overset{}{\underset{OH}{CH}} \overset{}{\underset{R^{3}}{N}} S[O]_x-R^4$$

wherein:

x represents 0, 1 or 2;

t represents either 0 or 1;

R$^1$ represents hydrogen, —CH$_2$SO$_2$NH$_2$, —CO$_2$CH$_3$, —CONHCH$_3$, —CON(CH$_3$)$_2$, —CH$_2$C(O)NHCH$_3$, —CH$_2$C(O)N(CH$_3$)$_2$, —CONH$_2$, —C(CH$_3$)$_2$(SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, o-alkyl serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from halogen and alkyl radicals, —$NO_2$, —C≡N, $CF_3$, —$OR^9$ and —$SR^9$, wherein R9 represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and $C(R^{17})$ wherein $R^{17}$ represents hydrogen and alkyl radicals;

Y and Y' independently represent O, S and $NR^{15}$ wherein $R^{15}$ represents hydrogen and radicals as defined for $R^3$;

$R^4$ represents radicals as defined by $R^3$ except for hydrogen;

$R^6$ represents hydrogen and alkyl radicals;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{30}$ and $R^{32}$ together with the carbon atoms to which they are attached form a three to six-membered cycloalkyl radical; and $R^{33}$ and $R^{34}$ independently represent hydrogen, radicals as defined for $R^3$, or $R^{33}$ and $R^{34}$ together with X' represent cycloalkyl, aryl, heterocyclyl and heteroaryl radicals, provided that when X' is O, $R^{34}$ is absent.

4. Method of inhibiting a retroviral protease comprising administering a protease inhibiting amount of a composition comprising (1) a compound of the following formula, or a pharmaceutically acceptable salt or ester thereof, and (2) a pharmaceutically acceptable carrier:

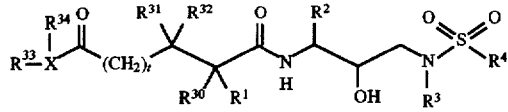

wherein:

t represents either 0 or 1;

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SH)$, —$C(CH_3)_2(SCH_3)$, —$C(CH_3)2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, —$NO_2$, —C≡N, $CF_3$, —$OR^9$, —$SR^9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and $C(R^{17})$ wherein $R^{17}$ represents hydrogen and alkyl radicals;

$R^4$ represents radicals as defined by $R^3$ except for hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{31}$ and $R^{32}$ together with the carbon atoms to which they are attached form a three to six-membered cycloalkyl radical; and $R^{33}$ and $R^{34}$ independently represent hydrogen and radicals as defined for $R^3$, or $R^{33}$ and $R^{34}$ together with X' represent cycloalkyl, aryl, heterocyclyl and heteroaryl radicals, provided that when X' is O, $R^{34}$ is absent.

5. Method of treating a retroviral infection comprising administering an effective amount of a composition comprising (1) a compound of the following formula, or a pharmaceutically acceptable salt or ester thereof, and (2) a pharmaceutically acceptable carrier:

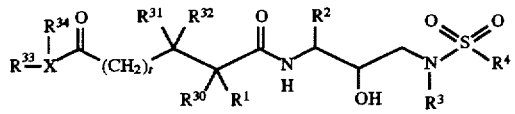

wherein:

t represents either 0 or 1;

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, —$NO_2$, —C≡N, $CF_3$, —$OR^9$, —$SR^9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and C($R^{17}$) wherein $R^{17}$ represents hydrogen and alkyl radicals;

$R^4$ represents radicals as defined by $R^3$ except for hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{31}$ and $R^{32}$ together with the carbon atoms to which they are attached form a three to six-membered cycloalkyl radical; and $R^{33}$ and $R^{34}$ independently represent hydrogen and radicals as defined for $R^3$, or $R^{33}$ and $R^{34}$ together with X' represent cycloalkyl, aryl, heterocyclyl and heteroaryl radicals, provided that when X' is O, $R^{34}$ is absent.

6. Method of treating AIDS comprising administering an effective amount of a composition comprising (1) a compound of the following formula, or a pharmaceutically acceptable salt or ester thereof, and (2) a pharmaceutically acceptable carrier:

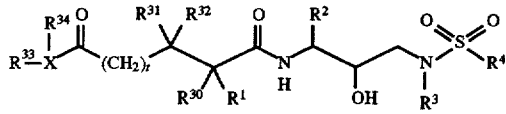

wherein:

t represents either 0 or 1;

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SH)$, —$C(CH_3)_2(SCH_3)$, —$C(CH_3)_2(S[O]CH_3)$, —$C(CH_3)2$ $(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, —$NO_2$, —C≡N, $CF_3$, —$OR^9$, —$SR_9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

X' represents N, O, and C($R^{17}$) wherein $R^{17}$ represents hydrogen and alkyl radicals;

$R^4$ represents radicals as defined by $R^3$ except for hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{31}$ and $R^{32}$ together with the carbon atoms to which they are attached form a three to six-membered cycloalkyl radical; and $R^{33}$ and $R^{34}$ independently represent hydrogen and radicals as defined for $R^3$, or $R^{33}$ and $R^{34}$ together with X' represent cycloalkyl, aryl, heterocyclyl and heteroaryl radicals, provided that when X' is O, $R^{34}$ is absent.

7. Method of inhibiting a retroviral protease comprising administering a protease inhibiting amount of a composition comprising (1) a compound of the following formula, or a pharmaceutically acceptable salt or ester thereof, and (2) a pharmaceutically acceptable carrier:

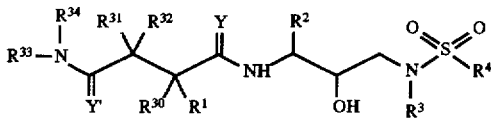

wherein:

$R^1$ represents hydrogen, —$CH_2SO_2NH_2$, —$CO_2CH_3$, —$CONHCH_3$, —$CON(CH_3)_2$, —$CH_2C(O)NHCH_3$, —$CH_2C(O)N(CH_3)_2$, —$CONH_2$, —$C(CH_3)_2(SH)$, —$C(CH_3)_2(SCH_3)$, —$C(CH_3)_2(S[O]CH_3)$, —$C(CH_3)2$ $(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl, and aralkyl radicals, which radicals are optionally substituted with a group selected from halogen and alkyl radicals, —$NO_2$, —C≡N, $CF_3$, —$OR^9$ and —$SR^9$ wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

$R^4$ represents radicals as defined by $R^3$ except hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; and $R^{33}$ and $R^{34}$ independently represent hydrogen and radicals as defined for $R^3$, or $R^{33}$ and $R^{34}$ together with the nitrogen atom to which they are attached represent heterocycloalkyl and heteroaryl radicals; and Y and Y' independently represent O, S, and $NR^{15}$ wherein $R^{15}$ represents hydrogen and radicals as defined for $R^3$.

8. Method of treating a retroviral infection comprising administering an effective amount of a composition comprising (1) a compound of the following formula, or a pharmaceutically acceptable salt or ester thereof, and (2) a pharmaceutically acceptable carrier:

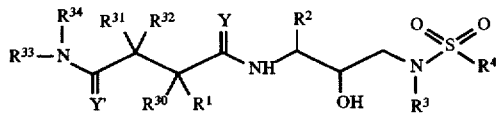

wherein:

$R^1$ represents hydrogen, $-CH_2SO_2NH_2$, $-CO_2CH_3$, $-CONHCH_3$, $-CON(CH_3)_2$, 13 $CH_2C(O)NHCH_3$, $-CH_2C(O)N(CH_3)_2$, $-CONH_2$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl, and aralkyl radicals, which radicals are optionally substituted with a group selected from halogen and alkyl radicals, $-NO_2$, $-C\equiv N$, $CF_3$, $-OR^9$ and $-SR^9$ wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

$R^4$ represents radicals as defined by $R^3$ except hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; and $R^{33}$ and $R^{34}$ independently represent hydrogen and radicals as defined for $R^3$, or $R^{33}$ and $R^{34}$ together with the nitrogen atom to which they are attached represent heterocycloalkyl and heteroaryl radicals; and Y and Y' independently represent O, S, and $NR^{15}$ wherein $R^{15}$ represents hydrogen and radicals as defined for $R^3$.

9. Method for treating AIDS comprising administering an effective amount of a composition comprising (1) a compound of the following formula, or a pharmaceutically acceptable salt or ester thereof, and (2) a pharmaceutically acceptable carrier:

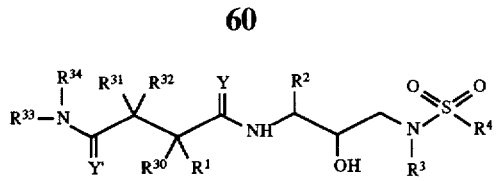

wherein:

$R^1$ represents hydrogen, $-CH_2SO_2NH_2$, $-CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl, and aralkyl radicals, which radicals are optionally substituted with a group selected from halogen and alkyl radicals, $-NO_2$, $-C\equiv N$, $CF_3$, $-OR^9$ and $-SR^9$ wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

$R^4$ represents radicals as defined by $R^3$ except hydrogen;

$R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; and $R^{33}$ and $R^{34}$ independently represent hydrogen and radicals as defined for $R^3$, or $R^{33}$ and $R^{34}$ together with the nitrogen atom to which they are attached represent heterocycloalkyl and heteroaryl radicals; and Y and Y' independently represent O, S, and $NR^{15}$ wherein $R^{15}$ represents hydrogen and radicals as defined for $R^3$.

10. Method of inhibiting a retroviral protease comprising administering a protease inhibiting amount of a composition comprising (1) a compound of the following formula, or a pharmaceutically acceptable salt or ester thereof, and (2) a pharmaceutically acceptable carrier:

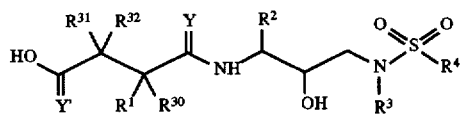

wherein:

$R^1$ represents hydrogen, $-CH_2SO_2NH_2$, $-CO_2CH_3$, $-CH_2CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C \equiv N$, $CF_3$, $-OR^9$, $-SR^9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

Y and Y' independently represent O, S and $NR^{15}$ wherein $R^{15}$ represents hydrogen and radicals as defined for $R^3$;

$R^4$ represents radicals as defined by $R^3$ except for hydrogen; and $R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{30}$ and $R^{32}$ together with the carbon atoms to which they are attached form a cycloalkyl radical.

11. Method of treating a retroviral infection comprising administering an effective amount of a composition comprising (1) a compound of the following formula, or a pharmaceutically acceptable salt or ester thereof, and (2) a pharmaceutically acceptable carrier:

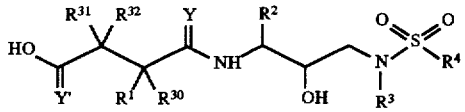

wherein:

$R^1$ represents hydrogen, $-CH_2SO_2NH_2$, $-CO_2CH_3$, $-CH_2CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SH)$, $-C(CH_3)_2(SCH_3)$, $-C(CH_3)_2(S[O]CH_3)$, $-C(CH_3)2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C \equiv N$, $CF_3$, $-OR^9$, $-SR^9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

Y and Y' independently represent O,S and $NR^{15}$ wherein $R^{15}$ represents hydrogen and radicals as defined for $R^3$;

$R^4$ represents radicals as defined by $R^3$ except for hydrogen; and $R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{30}$ and $R^{32}$ together with the carbon atoms to which they are attached form a cycloalkyl radical.

12. Method for treating AIDS comprising administering an effective amount of a composition comprising (1) a compound of the following formula, or a pharmaceutically acceptable salt or ester thereof and (2) a pharmaceutically acceptable carrier:

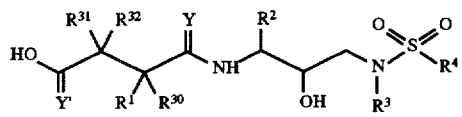

wherein:

$R^1$ represents hydrogen, $-CH_2SO_2NH_2$, $-CO_2CH_3$, $-CH_2CO_2CH_3$, $-CONHCH_3$, $-CON(CH_3)_2$, $-CH_2C(O)NHCH_3$, $-CH_2C(O)N(CH_3)_2$, $-CONH_2$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, ornithine, alanine, histidine, norleucine, glutamine, valine, threonine, serine, aspartic acid, beta-cyano alanine, and allothreonine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C \equiv N$, $CF_3$, $-OR^9$, $-SR^9$, wherein $R^9$ represents hydrogen and alkyl radicals;

$R^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

Y and Y' independently represent O, S and $NR^{15}$ wherein $R^{15}$ represents hydrogen and radicals as defined for $R^3$;

$R^4$ represents radicals as defined by $R^3$ except for hydrogen; and $R^{30}$, $R^{31}$ and $R^{32}$ represent radicals as defined for $R^1$, or one of $R^1$ and $R^{30}$ together with one of $R^{31}$ and $R^{32}$ and the carbon atoms to which they are attached form a cycloalkyl radical; or $R^{30}$ and $R^{32}$ together with the carbon atoms to which they are attached form a cycloalkyl radical.

13. Method of claim 1 wherein the retroviral protease is HIV protease.

14. Method of claim 2 wherein the retroviral infection is an HIV infection.

15. Method of claim 4 wherein the retroviral protease is HIV protease.

16. Method of claim 5 wherein the retroviral infection is an HIV infection.

17. Method of claim 7 wherein the retroviral protease is HIV protease.

18. Method of claim 18 wherein the retroviral infection is an HIV infection.

19. Method of claim 10 wherein the retroviral protease is HIV protease.

20. Method of claim 11 wherein the retroviral infection is an HIV infection.

* * * * *